United States Patent [19]

Wenger

[11] 4,249,001

[45] Feb. 3, 1981

[54] PROSTANOIC ERGOLIN-8-YL ESTERS, THIOESTERS, AND AMIDES

[75] Inventor: Roland Wenger, Riehen, Switzerland

[73] Assignee: Sandoz Ltd., Basel, Switzerland

[21] Appl. No.: 55,802

[22] Filed: Jul. 9, 1979

Related U.S. Application Data

[63] Continuation of Ser. No. 773,663, Mar. 2, 1977, abandoned.

[30] Foreign Application Priority Data

Apr. 27, 1976 [CH] Switzerland ............... 5268/76
Feb. 18, 1977 [CH] Switzerland ............... 2059/77

[51] Int. Cl.³ ............... C09B 23/00; C07D 457/00
[52] U.S. Cl. ............... 542/404; 546/67; 546/69; 544/182; 544/235; 544/253
[58] Field of Search ............... 542/404; 546/67, 69; 544/182, 235, 253

[56] References Cited

U.S. PATENT DOCUMENTS

| | | | |
|---|---|---|---|
| 3,940,387 | 2/1976 | Saint-Ruf et al. | 542/404 |
| 3,996,228 | 12/1976 | Arcari et al. | 546/67 X |

*Primary Examiner*—Paul F. Shaver
*Attorney, Agent, or Firm*—Gerald D. Sharkin; Robert S. Honor; Timothy G. Rothwell

[57] ABSTRACT

Prostanoic acid ergolinylalkyl-esters, -thioesters and -amides have interesting prostaglandin-like activity, especially blood pressure lowering activity.

27 Claims, No Drawings

PROSTANOIC ERGOLIN-8-YL ESTERS, THIOESTERS, AND AMIDES

This is a continuation, of application Ser. No. 773,663 filed Mar. 2, 1977, now abandoned.

This invention relates to prostaglandins and in particular provides prostanoic ergolin-8-ylalkyl-esters-, thioesters and -amides.

It is to be appreciated that the term prostanoic acid covers any natural or synthetic prostaglandin acid, and the term ergoline covers any natural or synthetic ergoline derivative.

The present invention provides especially compounds of formula I,

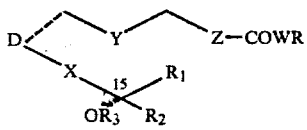

wherein D is a group of formula

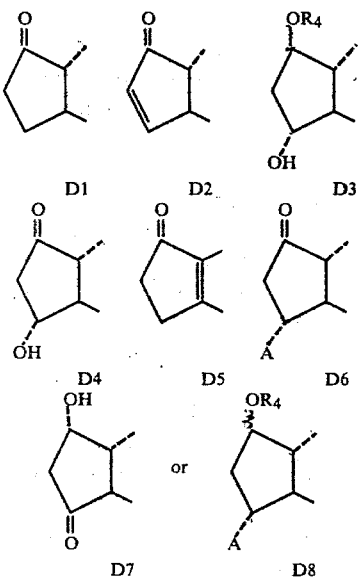

wherein A is a radical of formula (a),

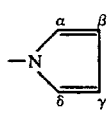

wherein 1 to 3 of the four methine groups marked $\alpha, \beta, \gamma$ and $\delta$ are replaced by nitrogen, or a radical of formula (b),

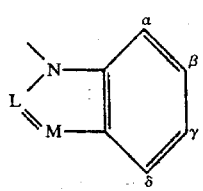

wherein either one of the ring members L and M is nitrogen and the other of the ring members L and M is methine, or each of L and M is nitrogen, 1 to 3 of the methine groups marked $\alpha, \beta, \gamma$ and $\delta$ may be replaced by nitrogen, and the six-membered ring is unsubstituted or mono-substituted by halogen, alkylamino, dialkylamino, alkoxy or alkylthio, each alkyl moiety of the last four radicals being independently of 1 to 5 carbon atoms, W is oxygen, sulphur or imino, X is —CH$_2$—CH$_2$— or —CH=CH—(trans), Y is —CH$_2$—CH$_2$— or —CH=CH—(cis or trans), Z is

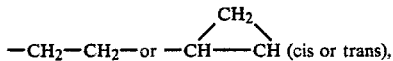

$R_1$ is alkyl of 1 to 10 carbon atoms or cycloalkyl of 3 to 9 carbon atoms, $R_2$ is hydrogen or alkyl of 1 to 7 carbon atoms, $R_3$ and $R_4$ are, independently, hydrogen, alkanoyl of 1 to 20 carbon atoms, or benzoyl, and R is an ergolinylalkyl radical of formula II,

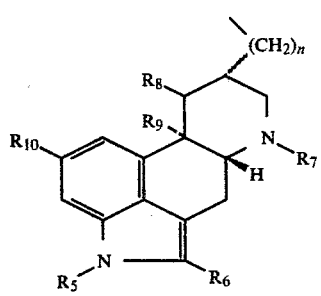

wherein n is 1 or 2, $R_5$ is hydrogen, alkyl of 1 to 4 carbon atoms, or benzyl, $R_6$ and $R_{10}$ are, independently, hydrogen or halogen, $R_7$ is alkyl of 1 to 4 carbon atoms other than tert.-butyl, and (i) each of $R_8$ and $R_9$ is hydrogen, or (ii) $R_8$ and $R_9$ together form a bond, or (iii) $R_8$ is hydrogen, and $R_9$ is alkoxy of 1 to 4 carbon atoms.

In formula I the 15-OR$_3$ group has the $\alpha$- or $\beta$-configuration, and the side chain in the 8 position of the ergolinylalkyl radical has the $\alpha$- or $\beta$-configuration.

Halogen is chlorine or bromine, preferably chlorine.

When A is a radical of formula (a), this is, for example, pyrazolyl, imidazolyl, triazolyl, e.g. 1,2,4-triazol-1-yl, or tetrazolyl, e.g. 1,2,3,4-tetrazol-1-yl.

When A is a radical of formula (b), preferably 0, 1 or 2 methine groups, as defined above, of the six-membered ring are replaced by nitrogen. Preferably M is nitrogen. Preferred examples of such radicals are benzimidazolyl or purinyl. The radical of formula (b) is preferably unsubstituted. When it is mono-substituted the ring has preferably a substituent attached to a carbon atom in the ring position marked $\alpha$ or $\delta$. The alkyl of the ring substituents defined above preferably have 1 or 2 carbon atoms, especially one carbon atom. The preferred ring substituent is the dialkylamino group.

When $R_1$ is alkyl, this preferably has 5 to 8 carbon atoms. It is conveniently branched in the $\alpha$-position.

Suitable examples are 1-pentyl; 2-methyl-2-hexyl; 2-hexyl; 1-heptyl, or 2-octyl.

When $R_1$ is cycloalkyl, this preferably is cyclopentyl or cyclohexyl.

When $R_3$ is alkanoyl, this preferably has 2 to 5 carbon atoms, and is conveniently acetyl.

When $R_4$ is alkanoyl, this preferably has 8 to 20 carbon atoms, and is conveniently n-octanoyl or lauroyl.

When $R_5$ is alkyl, this is conveniently methyl.

When $R_7$ is alkyl, this has conveniently 1 to 3 carbon atoms, and is conveniently methyl or isopropyl.

When $R_9$ is alkoxy, this is conveniently methoxy.

Preferred significances in the prostanoic moiety are as follows:

D is D4 or D6,
A is imidazolyl,
W is oxygen or imino,
X is $-CH=CH-$(trans),
Y is $-CH=CH-$(cis) or $-CH_2-CH_2-$,
Z is

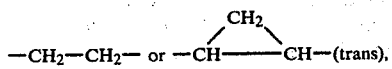

$-CH_2-CH_2-$ or $-CH \underset{CH_2}{\overline{\phantom{XX}}} CH-$(trans), $R_1$ is alkyl,
$R_2$, $R_3$ and $R_4$ are hydrogen,
the $-OR_3$ group is in the α-configuration.

Preferred significances in the ergolinylalkyl moiety are as follows:
n is 1;
$R_5$ is hydrogen or methyl;
$R_7$ is methyl;
(i) $R_8$, $R_9$, $R_6$ and $R_{10}$ are each hydrogen, or
(ii) $R_8$ and $R_9$ are together a bond and each of $R_6$ and $R_{10}$ is hydrogen, or
(iii) $R_8$, $R_9$ and $R_{10}$ are each hydrogen and $R_6$ is bromine,
(iv) $R_8$ and $R_9$ are each hydrogen, and $R_6$ and $R_{10}$ are each bromine;
(v) $R_8$ and $R_9$ are together a bond, $R_6$ is bromine and $R_{10}$ is hydrogen.

The present invention provides a process for the production of an ester, thioester or amide as defined above, which comprises condensing a prostanoic acid or a reactive functional acid derivative thereof with a 8-hydroxyalkylergoline, 8-thioalkylergoline or 8-aminoalkylergoline.

In particular the invention provides a process for the production of a compound of formula I, as defined above, which comprises
(a) for the production of a compound of formula I, condensing a compound of formula III,

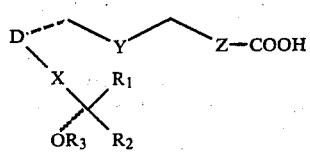   III wherein D, $R_1$, $R_2$, $R_3$, X, Y and Z are as defined above, or a reactive functional acid derivative thereof, with a compound of formula IV, $H-WR$    IV wherein R and W are as defined above, or (b) for the production of a compound of formula Ia,

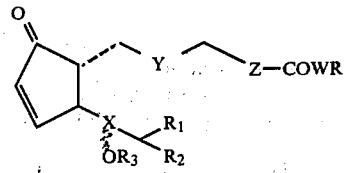   Ia wherein R, $R_1$, $R_2$, $R_3$, W, X, Y and Z are as defined above, splitting off HA from a compound of formula Ib,

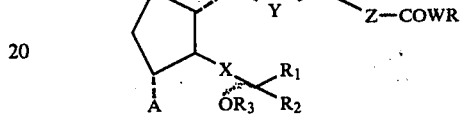   Ib wherein A, R, $R_1$, $R_2$, $R_3$, W, X, Y and Z are as defined above.

Process (a) may be effected in conventional manner for the production of esters, thioesters and amides of prostanoic acids, bearing in mind the nature of the reactants.

Conveniently a reactive functional acid derivative is produced in situ using N,N'-carbonyldiimidazole and a prostanoic acid. In order to activate an hydroxylalkylergoline or thioalkylergoline conveniently a catalytic amount of a solution of sodium imidazole in tetrahydrofuran is present.

When a compound of formula III is used, wherein D is D2, the imidazolyl formed in situ may lead to an end product of formula I, wherein D is D6 and A is imidazolyl.

For the production of a compound of formula I, wherein D is D2, and for an alternative preparation of amides, other reactive functional acid derivatives, e.g. the 2-thiopyridyl derivative, are preferably used.

Process (b) is preferably effected in the presence of an alkanol, e.g. methanol. Suitable temperatures are from about 0° C. to about 50° C., for example room temperature. The reaction time is in general from 2 to 30 hours for a satisfactory yield. The process may be effected in an inert organic solvent, e.g. tetrahydrofuran or methylene chloride. The process may be effected in water as solvent. At a pH of more than 7, e.g. up to 9, the reaction may proceed quicker than at below 7. Sodium bicarbonate, potassium bicarbonate, sodium acetate or a tertiary amine, e.g. pyridine or triethylamine may be present to afford a suitable pH.

Process (b) is the preferred process for the production of a compound of formula Ia, especially when W is oxygen or sulphur.

The present invention also provides a process [process (c)] for the production of a compound of formula IIIa,

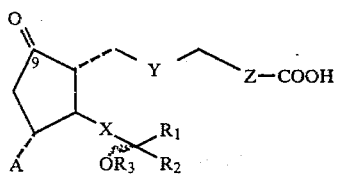

IIIa wherein A, $R_1$, $R_2$, $R_3$, X, Y and Z are as defined above, which comprises aminating a compound of formula IIIb,

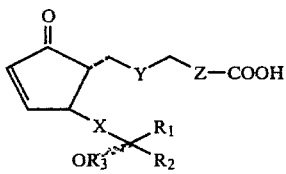

IIIb wherein $R_1$, $R_2$, $R_3$, X, Y and Z are as defined above.

Process (c) may be effected in conventional manner for analogous aminations. The reaction is conveniently effected at a temperature of from 0° to 40° C., preferably room temperature, in an inert organic solvent.

In certain instances, e.g. when A is purine, an isomerization of the amine may take place, so that 2 final products of formula III are produced, [see, for example, Example 4].

There is also provided a process for the production of a compound of formula III, wherein D is D8, which comprises (d) for the production of a compound of formula III, wherein D is D8 and one of the substituents $R_3$ and $R_4$ is hydrogen, and the other is alkanoyl of 1 to 20 carbon atoms or benzoyl, splitting off a protecting group from a compound of formula V,

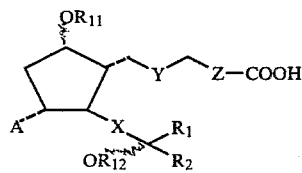

V wherein A, $R_1$, $R_2$, X, Y and Z are as defined above, and one of the substituents $R_{11}$ and $R_{12}$ is an alkanoyl group of 1 to 20 carbon atoms or benzoyl, and the other is a protecting group, (e) for the production of a compound of formula III, wherein D is D8 and at least one of the substituents $R_3$ and $R_4$ is alkanoyl of 1 to 20 carbon atoms or benzoyl, acylating a compound of formula III, wherein D is D8 and at least one of the substituents is hydrogen, or (f) for the production of a compound of formula IIIc,

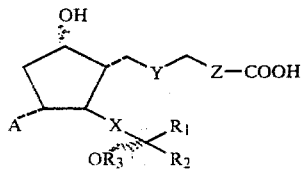

IIIc wherein A, $R_1$, $R_2$, $R_3$, X, Y and Z are as defined above, reducing selectively the carbonyl group of a compound of formula IIIa as defined above.

Process (d) may be effected in conventional manner for the splitting off of suitable protecting groups, e.g. tetrahydro-2H-pyran-2-yl, in the prostaglandin art, as described in Example 6e.

Process (e) may be effected in conventional manner for acylation of analogous compounds, as described in Example 6d.

Process (f) may be effected in conventional manner for reduction of analogous compounds, e.g. using sodium borohydride, as described in Example 6c. The resulting 9α and 9β isomers may be separated in conventional manner.

Preferably all the above-mentioned reactions are effected using pure starting materials and reagents, e.g. in anhydrous form. Preferably a nitrogen atmosphere is used.

The prostaglandins are purified in conventional manner.

Free base forms of the compounds of formula I and compounds of formula III, wherein D is D6 or D8, may be converted into acid addition salt forms and vice versa. Suitable acids for salt formation include tartaric acid and methanesulphonic acid.

The prostaglandins may exist in racemic or optically active form. The optically active forms may be produced in conventional manner, e.g. from optically active starting materials.

Insofar as the production of any starting material is not particularly described this may be prepared in known manner, or analogous to know processes or to processes described herein.

In the following Examples all temperatures are in degrees Centigrade and are uncorrected.

I.R. refers to characteristic bands of a sample in methylene chloride solution, unless stated otherwise. N.M.R. spectrum may be used to confirm the structures of the compounds obtained.

The usual vacuum used is 10 mm Hg., and the usual high vacuum 0.1 mm Hg. "lysergyl" refers to 6-methyl-9,10-didehydro-8β-hydroxymethylergoline.

Unless otherwise stated, the exemplified compounds are optically active and have absolute configurations at C-8 and C-12 identical to the respective configurations at C-8 and C-12 in prostanoic acid. cis or trans −(+) or (−) methylene as used hereinafter to the respective (+) or (−) optical isomer of cis or trans 2-(2'-bromoethyl)-cycloprop-1-ylcarboxylic acid, which may be used in the synthesis of the corresponding optically active compound of formula III, wherein Z is

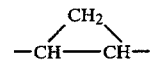

using conventional stereospecific procedures.

EXAMPLE 1:

11α,15S-Dihydroxy-9-keto-13-trans-prostenoic acid dihydroisolysergyl amide [process (a)]

A solution of 150 mg pure prostaglandin E in 4 ml absolute dimethylformamide is treated with 76 mg N,N'-carbonyldiimidazole and is stirred for 3½ hours at room temperature. 130 mg finely powdered dihydroisolysergylamine is added. After stirring for 7 days, the solvent is removed under high vacuum at room temperature and the oily residue is chromatographed on 250 g Sephadex LH20 with methylene chloride +1% methanol as eluant to yield the title compound in free base form.

I.R.: 1740, 1660, 1520 cm$^{-1}$

The free base is converted by treatment with methanesulphonic acid into the methanesulphonate salt form.

PRODUCTION OF ESTERS

In analogous manner to that described in Example 1 using the appropriate prostaglandin of formula III and compound of formula IV, wherein W is oxygen, together with a catalytic amount of sodium imidazole in tetrahydrofuran, there are obtained the following esters of formula I:

(a) 9α,11α,15S-trihydroxy-5-cis,13trans-prostadienoic acid lysergyl ester; M.Pt. of hydrogen tartrate 117°–120°;
(b) 11α,15S-dihydroxy-9-keto-13trans-prostenoic acid lysergyl ester; M.Pt. of hydrogen tartrate 158°–160°;
(c) 11α,15S-dihydroxy-9-keto-13trans-prostenoic acid (2',13'-dibromo)dihydrolysergyl ester,
I.R.: 1740 (broad) cm$^{-1}$
(d) 11α,15S-dihydroxy-9-keto-5cis,13trans-prostadienoic acid lysergyl ester;
I.R.: 1740 (broad) cm$^{-1}$
(e) 11α,15S-dihydroxy-9-keto-13trans-prostenoic acid (1'-methyl)lysergyl ester;
I.R.: 1740, 1735 (shoulder) cm$^{-1}$
(f) 11α,15S-dihydroxy-9-keto-13trans-prostenoic acid (10'α-methoxy)dihydrolysergyl ester;)
I.R.: 1740 (broad) cm$^{-1}$
(g) 11α,15S-dihydroxy-9-keto-13trans-prostenoic acid 2-(2'-chloro-6'-methylergolin-8'β-yl)ethyl ester;
I.R.: 1740, 1735 cm$^{-1}$
(h) 11α,15S-dihydroxy-9-keto-15-methyl-2,3trans-(-)-methylene-13trans-prostenoic acid lysergyl ester;
I.R.: 1740, 1730 cm$^{-1}$
(i) 11α,15S-dihydroxy-9-keto-15-methyl-5cis,13trans-prostadienoic acid lysergyl ester;
I.R.: 1745, 1735 (shoulder) cm$^{-1}$
(j) 11α,15S-dihydroxy-9-keto-prostanoic acid lysergyl ester;
I.R.: 1740 (broad) cm$^{-1}$
(k) 11α,15R-dihydroxy-9-keto-16R-methyl-5cis-prostenoic acid lysergyl ester;
I.R.: 1740, 1735 (shoulder) cm$^{-1}$
(l) 11α,15R-dihydroxy-9-keto-16R-methyl-2,3trans-(+)-methylene-5cis-prostenoic acid lysergyl ester;
I.R.: 1740, 1735 (shoulder) cm$^{-1}$
(m) 15-cyclohexyl-11α,15R-dihydroxy-9-keto-16,17,18,19,20-pentanor-5cis-prostenoic acid lysergyl ester;
I.R.: 1740 (broad) cm$^{-1}$
(n) 11α,15R-dihydroxy-9-keto-16R-methyl-2,3trans-(-)-methylene-5cis-prostenoic acid lysergyl ester;
I.R.: 1740, 1735 (shoulder) cm$^{-1}$.

In analogous manner to that described in Example 1 and using, when A is imidazole, the appropriate prostaglandin of formula III, wherein D is D2 in the presence of imidazole, or the appropriate prostaglandin of formula III, wherein D is D6 and appropriate compound of formula IV, wherein W is oxygen together with a catalytic amount of sodium imidazole in tetrahydrofuran, the following esters of formula I, wherein D is D6, are produced:

(aa) 15S-hydroxy-11α-imidazol-1'-yl-9-keto-5cis,13-trans-prostadienoic acid lysergyl ester;
I.R.: 3450, 1740, 1730 cm$^{-1}$ (ab) 15R-hydroxy-11α-imidazol-1'-yl-9-keto-5cis,13-trans-prostadienoic acid lysergyl ester;
I.R.: 3550, 3450, 1745-1740 cm$^{-1}$
(ac) 15S-hydroxy-11α-imidazol-1'-yl-9-keto-13trans-prostenoic acid lysergyl ester, M.Pt. of hydrogen tartrate 104°–106°;
(ad) 15S-hydroxy-11α-imidazol-1'-yl-9-keto-5cis,13-trans-prostadienoic acid dihydroisolysergyl ester;
I.R.: 3450, 1740, 1720, 1500 cm$^{-1}$
(ae) 15S-hydroxy-11α-imidazol-1'-yl-9-keto-5cis,13-trans-prostadienoic acid (2',13'-dibromo)dihydrolysergyl ester;
I.R.: 3450, 1740, 1715, 1500 cm$^{-1}$
(af) 15S-hydroxy-9-keto-1',2',4'-triazol-1'-yl-5cis,13-trans-prostadienoic acid lysergyl ester;
I.R.: 1740, 1720 cm$^{-1}$
(ag) 15R-hydroxy-11α-imidazol-1'-yl-9-keto-16R-methyl-5cisprostenoic acid lysergyl ester;
I.R.: 1740, 1720, 1500 cm$^{-1}$
(ah) 15S-hydroxy-11α-imidazol-1'-yl-9-keto-5cis,13-trans-prostadienoic acid (1'-methyl)lysergyl ester
I.R.: 1740, 1725 cm$^{-1}$
(ai) 15-cyclohexyl-15R-hydroxy-11α-imidazol-1'-yl-9-keto-16,17,18,19,20-pentanor-5cis,13trans-prostadienoic acid lysergyl ester;
I.R.: 1740, 1720 cm$^{-1}$
(aj) 15R-hydroxy-11α-imidazol-1'-yl-9-keto-16R-methyl-2,3trans-(-)-methylene-5cis-prostenoic acid lysergyl ester;
I.R.: 1740, 1720 cm$^{-1}$
(ak) 15S-hydroxy-11α-imidazol-1'-yl-9-keto-13trans-prostenoic acid (2',13'-dibromo)dihydrolysergyl ester;
I.R.: 1740, 1715, 1500 cm$^{-1}$.
(al) 15R-hydroxy-11α-imidazol-1'-yl-9-keto-5cis,13-trans-prostadienoic acid dihydroisolysergyl ester;
I.R.: 3450, 1740, 1720, 1500 cm$^{-1}$.

PRODUCTION OF THIOESTERS

In analogous manner to that described in Example 1 using the appropriate prostaglandin of formula III and thiol of formula IV together with a catalytic amount of sodium imidazole in tetrahydrofuran, the following compounds of formula I are produced:

(ba) 11α,15S-dihydroxy-9-keto-13trans-prostenoic acid lysergyl thioester;
I.R.: 1740, 1695 cm$^{-1}$
(bb) 15S-hydroxy-11α-imidazol-1'-yl-9-keto-5cis,13-trans-prostadienoic acid lysergyl thioester (starting from prostaglandin A$_2$);
I.R.: 1740, 1700 cm$^{-1}$

PRODUCTION OF AMIDES

In analogous manner to that described in Example 1 using the appropriate prostaglandin of formula III and the appropriate amine of formula IV the following amides of formula I are produced:

(ca) 11α,15S-dihydroxy-9-keto-13trans-prostenoic acid lysergyl amide;
I.R.: (CH$_2$Cl$_2$+CH$_3$OH): 3400 (broad), 1740, 1660, 1520 cm$^{-1}$
(cb) 11α,15S-dihydroxy-9-keto-13trans-prostenoic acid dihydrolysergyl amide;
I.R.: 1740, 1665, 1520 cm$^{-1}$
(cc) 11α,15S-dihydroxy-9-keto-13trans-prostenoic acid 2-(6'-methylergolin-8'β-yl)ethyl amide;
I.R.: 3400, 1740, 1660, 1520 cm$^{-1}$
(cd) 11α,15R-dihydroxy-9-keto-16R-methyl-2,3trans-(-)-methylene-5cis-prostenoic acid lysergyl amide;
I.R.: 1740, 1665, 1520 cm$^{-1}$ (ce) 9α,11α,15S-trihydroxy-5cis,13trans-prostadienoic acid lysergyl amide;
I.R.: 1660, 1520 cm$^{-1}$ (cf) 11α,15S-dihydroxy-9-keto-prostanoic acid lysergyl amide;
I.R.: (CH$_2$Cl$_2$+CH$_3$OH): 3400 (broad), 1740, 1660, 1520 cm$^{-1}$ (cg) 15S-hydroxy-9-keto-5cis,13trans-prostadienoic acid lysergyl amide;
I.R.: 1740, 1660, 1520 cm$^{-1}$ (ch) 15S-hydroxy-11α-imidazol-1'-yl-9-keto-5cis,13-trans-prostadienoic acid (1'-methyl)lysergyl amide;
I.R.: 1725, 1660, 1520 cm$^{-1}$ (ci) 15S-hydroxy-11α-imidazol-1'-yl-9-keto-5cis,13-trans-prostadienoic acid 2-(6'-methylergolin-8'β-yl)ethyl amide;
I.R.: 1725, 1665, 1525 cm$^{-1}$ (cj) 15S-acetoxy-11α-imidazol-1'-yl-9-keto-5cis,13trans-prostadienoic acid lysergyl amide;
I.R.: 1730 (broad), 1660, 1520 cm$^{-1}$ (ck) 15S-hydroxy-11α-imidazol-1'-yl-9-keto-5cis,13-trans-prostadienoic acid lysergyl amide;
I.R.: 3450, 1740, 1665, 1520 cm$^{-1}$ (cl) 15S-hydroxy-11α-imidazol-1'-yl-9-keto-13trans-prostenoic acid lysergyl amide;
I.R.: 1725, 1665, 1525 cm$^{-1}$.

Using the process described above esters, thioesters and amides of formula I, wherein R is lysergyl, dihydrolysergyl, isolysergyl, dihydroisolysergyl, 2-bromolysergyl, 13-bromodihydrolysergyl, 2,13-dibromodihydrolysergyl, 10α-methoxylsergyl, 10α-methoxydihydroisolysergyl, 2,13-dibromo-10α-methoxydihydrolysergyl, or 2- or 13-bromo-10α-methoxydihydrolysergyl and the prostanoic moiety is derived from
16,16-dimethyl PGE$_2$
16,16-dimethyl PGF$_{2α}$
15-methyl PGE$_2$
15-methyl PGF$_{2α}$
16R- and 16S-methyl-13,14-dihydro PGE$_2$
11-desoxy-PGE$_2$, the 15 epi isomer thereof, as well as the 5,6-dihydro or 5,6,13,14-tetrahydro derivative thereof, PGE$_2$, the 15-epi isomer, or the 5,6-dihydro or 5,6,13,14-tetrahydro derivative thereof,
PGF$_{1α}$, the 15-epi isomer, or the 13,14-dihydro derivative thereof may be obtained.

EXAMPLE 2:

15S-Hydroxy-9-keto-5cis,10cis,13trans-prostatrienoic acid lysergyl amide (a) 159 mg prostaglandin A$_2$ is stirred with 167 mg of 2,2-dithiopyridine and 199 mg triphenylphosphine in 5 ml xylene for 24 hours at 20°. The reaction mixture is concentrated to give an oil which is chromatographed on 100 g of Sephadex LH20 (eluant CH$_2$Cl$_2$+2% CH$_3$OH) to yield the 2-thiopyridyl ester of prostaglandin A$_2$.

(b) 131 mg of the 2-thiopyridyl ester of prostaglandin A$_2$ is stirred in 5 ml of tetrahydrofuran with 93 mg of lysergyl amine for 24 hours at 20°. The reaction mixture is chromatographed directly on Sephadex LH20 (eluant CH$_2$Cl$_2$+0.5% CH$_3$OH) to give the pure title compound.
I.R.: 3450, 1730, 1710 cm$^{-1}$.

In analogous manner the following compounds are produced:

(a) 15S-hydroxy-9-keto-10cis,13trans-prostadienoic dihydrolysergyl amide;
I.R.: 3450, 1705, 1665, 1520 cm$^{-1}$ (b) 15R-hydroxy-9-keto-16R-methyl-2,3trans-(−)-methylene-5,10cis-prostadienoic acid lysergyl amide;
I.R.: 3450, 1700, 1665, 1520 cm$^{-1}$.

As well as the compounds of Examples 1 and I (ca) to (cg).

EXAMPLE 3:

15S-hydroxy-9-keto-5,10cis,13trans-prostatrienoic acid lysergyl ester [process (b)]

248 mg of 15S-hydroxy-11α-imidazol-1'-yl-9-keto-5cis,13trans-prostadienoic acid lysergyl ester are maintained at room temperature in 9 ml of methanol for 30 hours. The methanol is removed under vacuum at room temperature. The oily residue is immediately worked up by chromatography on Sephadex LH20 (eluant: CH$_2$Cl$_2$+0.25% CH$_3$OH) to yield the title compound.
I.R.: 3450, 1730, 1710 cm$^{-1}$.

Analogous to Example 3, the following compounds are also obtained from the corresponding compound of formula IIIa, wherein A is imidazol-1-yl:

(a) 15R-hydroxy-9-keto-5,10cis,13trans-prostatrienoic acid lysergyl ester;
I.R.: 3560, 3350, 1720, 1695, 1600 cm$^{-1}$ (b) 15S-hydroxy-9-keto-5,10cis,13trans-prostatrienoic acid dihydrolysergyl ester;
I.R.: 3555, 3350, 1730, 1705 cm$^{-1}$, as well as the compounds of Examples 2 and 2(a)–(b).

EXAMPLE 4:

15S-hydroxy-9-keto-11α-purin-7'-yl-5cis,13trans-prostadienoic acid and
15S-hydroxy-9-keto-purin-9'-yl-5cis,13trans-prostadienoic acid [process (c)]

356 mg of prostaglandin A$_2$ and 127 mg of purine are dissolved in 4 ml of absolute dimethylformamide, and maintained at room temperature for 6 weeks. The progress of the reaction is followed by thin layer chromatography (eluant: CHCl$_3$/20% CH$_3$OH+1% CH$_3$COOH). After concentration of the reaction mixture at room temperature under a high vacuum, the resulting oil is chromatographed on Sephadex LH20 (eluant: CH$_2$Cl$_2$+1% CH$_3$OH). From this chromatography it is possible to obtain a mixture of the 11α-purin-7'-yl derivative and the 11α-purin-9'-yl derivative [mixture (a)] and a mixture of the 11α-purin-9'-yl derivative and prostaglandin A$_2$ [mixture (b)].

Mixture (a) is chromatographed twice more on Sephadex yielding pure 15S-hydroxy-9-keto-11α-purin-7'-yl-5cis,13trans-prostadienoic acid as the more polar product. I.R.: 1745, 1705, 1600, 1560 cm$^{-1}$.

148 mg of mixture (b) is treated with 23 mg imidazole and maintained at room temperature for 1½ hours. The reaction mixture is dissolved in 100 ml of methylene chloride and washed with 0.01 N hydrochloric acid. The organic phase is separated off, dried, filtered and concentrated to yield 15S-hydroxy-9-keto-11α-purin-9'-yl-5cis,13trans-prostadienoic acid. I.R.: 1745, 1705, 1600, 1580, 1500 cm$^{-1}$.

EXAMPLE 5:

15S-hydroxy-11α-imidazol-1'-yl-9-keto-5cis,13trans-prostadienoic acid [process (c)]

315 mg of prostaglandin A$_2$ and 96 mg imidazole are treated with 3 ml methylene chloride and maintained until a clear solution results. After evaporation of the solvent at room temperature the resultant oil is maintained at room temperature for 3 days and then chromatographed on Sephadex LH20 (eluant: $CH_2Cl_2 + 1\%$ $CH_3OH$) to afford the title compound.

I.R.: 3350, 3300, 1740, 1710, 1695 (shoulder), 1600 $cm^{-1}$.

In analogous manner to Example 5 the following compounds of formula IIIa are obtained:

(a) 15S-hydroxy-11α-imidazol-1'-yl-9-keto-13trans-prostenoic acid;
I.R.: 3450, 1740, 1710, 1695 (shoulder) $cm^{-1}$ (b) 15S-hydroxy-9-keto-11α-1',2',4'-triazol-1'-yl-5cis,13-trans-prostadienoic acid;
I.R.: 1745, 1705, 1505 $cm^{-1}$ (c) 15S-hydroxy-9-keto-11α-pyrazol-1'-yl-5cis,13trans-prostadienoic acid;
I.R.: 1745, 1705, 1505 (small) $cm^{-1}$ (d) 15R-hydroxy-9-keto-11α-(6'-dimethylamino)-purin-9'-yl-5cis,13trans-prostadienoic acid;
I.R.: 1745, 1705, 1600, 1560 $cm^{-1}$ (e) 15R-hydroxy-11α-imidazol-1'-yl-9-keto-5cis,13-trans-prostadienoic acid;
I.R.: 1740, 1700, 1500 $cm^{-1}$ (f) 16,16-dimethyl-15R-hydroxy-11α-imidazol-1'-yl-9-keto-2,3-trans-(−)-methylene-5cis,13trans-prostadienoic acid;
I.R.: 1740, 1700 $cm^{-1}$ (g) 15-S-hydroxy-9-keto-11α-(6'-dimethylamino)-purin-9'-yl-5cis,13trans-prostadienoic acid;
I.R.: 1745, 1705, 1600, 1565 $cm^{-1}$ (h) 11R-hydroxy-11α-imidazol-1'-yl-9-keto-16R-methyl-5cis-prostenoic acid;
I.R.: 1745, 1705, 1500 $cm^{-1}$ (i) 15S-acetoxy-11α-imidazol-1'-yl-9-keto-5cis,13trans-prostadienoic acid;
I.R.: 1745, 1735 (shoulder), 1700 $cm^{-1}$ (j) 15-cyclohexyl-11α-imidazol-1'-yl-15R-hydroxy-9-keto-16,17,18,19,20-pentanor-5cis,13trans-prostadienoic acid;
I.R.: 1740, 1700 $cm^{-1}$ (k) 15R-hydroxy-11α-imidazol-1'-yl-9-keto-16R-methyl-2,3-trans-(−)-methylene-5cis-prostenoic acid;
I.R.: 1740, 1700 $cm^{-1}$.

EXAMPLE 6: 15S-hydroxy-11α-imidazol-1'-yl-9α- and 9β-octanoyl-5cis,13trans-prostadienoic acid (a) 150 mg of prostaglandin $A_2$ is treated with one equivalent of dihydropyran in 10 ml of methylene chloride at 0° with a catalytic amount of para-toluene sulphonic acid. After working up the 15-tetrahydro-2H-furan-2-yl ether of prostaglandin $A_2$ is obtained.

(b) This ether was converted into 11α-imidazol-1'-yl-9-keto-15S-tetrahydro-2H-pyran-2'-yloxy-5cis,13trans-prostadienoic acid in analogous manner to Example 5.

(c) 180 mg of the 11α-imidazol-1'-yl-15S-tetrahydro-pyran-2'-yloxy compound is treated with 35 mg of sodium borohydride in 10 ml of dioxane at room temperature to yield on, working up, 9α-hydroxy-11α-imidazol-1'-yl-15S-(tetrahydro-2H-pyran-2'-yloxy)-5cis,13trans-prostadienoic acid and the 9β hydroxy analogue thereof.

(d) 300 mg of a mixture of the 9α and 9β hydroxy compounds obtained in step (c) in 10 ml acetone and 3 ml pyridine are treated at −10° with 0.4 ml n-octanoyl chloride in 10 ml in acetone. The reaction mixture is maintained for 16 hours, diluted with methylene chloride, washed with phosphate buffer and concentrated to afford a mixture of the 9α and 9β-n-octanoyloxy derivatives.

(e) To split off the tetrahydropyranyl group the 9α and 9β-n-octanoyloxy derivatives [obtained in step (d)] are treated with 4.5 ml of a mixture of acetic acid/water/acetone (1:1:1) and warmed to 60° for 30 minutes. The reaction mixture is worked up in conventional manner and chromatographed on Sephadex LH20 (eluant: $CH_2Cl_2 + 1\%$ $CH_3OH$) to give separately the 9α and 9β isomers of the title compound.

In analogous manner to that described in Example 1 there are obtained compounds of formula I, wherein D is D6, and A is

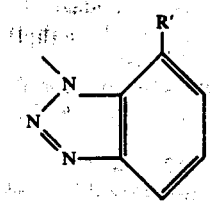

wherein
R' is n $C_3H_7NH—$
n $C_3H_7O$
n $C_3H_7S$
Cl, or
D is D1, D3 or D8, wherein the 9 side chain is β-benzoyloxy, D5, D7,
X is $—CH_2—CH_2—$, Y is $—CH_2—CH_2—$,
Z is

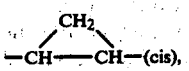

$R_1$ is $CH_3$ or n-$C_{10}H_{21}$,
$R_2$ is n-$C_7H_{15}$,
W is S,
R is 1-(n-$C_4H_9$) lysergyl or 1-(benzyl)lysergyl.

The above-defined ergolinylalkyl esters, thioesters and amides and compounds of formula III, wherein D is D6 or D8, exhibit pharmacological activity and are therefore useful in animals. In particular, they exhibit prostaglandin-like activity, especially a lowering of the arterial blood pressure and an inhibition of blood platelet aggregation.

The action of the compounds in inhibiting arterial blood pressure is indicated in standard tests, e.g. in the anaesthetized spontaneous hypertonic rat test or in the normotonic dog on i.v. administration of from 0.1 to 3 mg/kg animal body weight per day.

For the above-mentioned use the dosage will, of course, vary depending on the compound employed, mode of administration and therapy desired. However, in general, satisfactory results are obtained when administered at a daily dosage of from 0.1 μg to about 3 mg per kg animal body weight, conveniently given in divided doses 2 to 4 times a day or in sustained release form. For the larger mammal, the total daily dosage is in the range from about 10 to about 50 μg, and dosage forms suitable for oral administration comprise from about 2 μg to about 25 μg of the compounds admixed with a solid or liquid pharmaceutical carrier or diluent.

The action of the compounds in inhibiting blood platelet aggregation is indicated by in vitro tests, wherein an inhibition of rabbit plasma aggregation induced by adenosine phosphate or collagen is observed at a concentration of from 1 to 10 μg/ml.

The compounds also exhibit a uterotonic effect for stimulating smooth muscle, as indicated in standard in vitro tests on an isolated uterus muscle at a dose of from 1 to 10 μg.

The compounds also exhibit an inhibition of gastric secretion as indicated in standard tests, e.g. by an inhibition of pentagastrin induced secretion in rats at a dose of from 1 to 100 μg/kg.

For the above-mentioned use the dosage will, of course, vary depending on the compound employed, mode of administration and therapy desired. However, in general, satisfactory results are obtained when administered at a daily dosage of from 1 μg to about 100 μg per kg animal body weight, conveniently given in divided doses 2 to 4 times a day or in sustained release form. For the larger mammal, the total daily dosage is in the range from about 1 to about 20 mg, and dosage forms suitable for oral administration comprise from about 0.25 mg to about 10 mg of the compounds admixed with a solid or liquid pharmaceutical carrier or diluent.

The above defined ergolinylalkyl-esters, -thiesters and -amides and compounds of formula III, wherein D is D6 or D8, may be administered in pharmaceutically acceptable acid addition salt form. The present invention accordingly provides a pharmaceutical composition comprising a prostenoic acid ergolinylalkylester, -thioester or -amide or a compound of formula III, wherein D is D6 or D8, in free base form or in pharmaceutically acceptable acid addition salt form in association with a pharmaceutical carrier or diluent. Such compositions may be made in conventional manner so as to be, for example, a solution or tablet.

I claim:

1. A prostanoic ergolin-8-yl ester, -thioester and amide in free form or in pharmaceutically acceptably acid addition salt form.

2. A compound of claim 1 having the formula I,

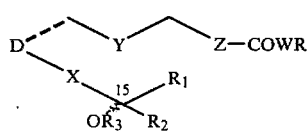

I wherein D is a group of formula

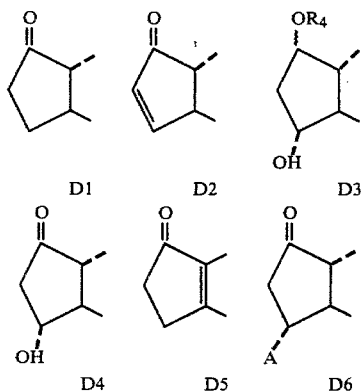

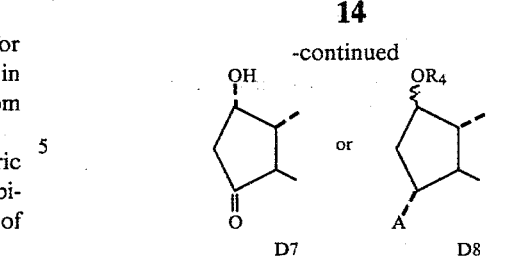

wherein A is a radical of formula (a),

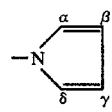

a wherein 1 to 3 of the four methine groups marked α, β, γ and δ are replaced by nitrogen, or a radical of formula (b),

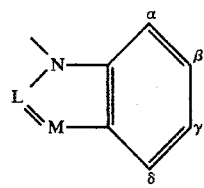

b wherein either one of the ring members L and M is nitrogen and the other of the ring members L and M is methine, or each of L and M is nitrogen, 1 to 3 of the methine groups marked α, β, γ and δ may be replaced by nitrogen, and the six-membered ring is unsubstituted or mono-substituted by halogen, alkylamino, dialkylamino, alkoxy or alkylthio, each alkyl moiety of the last four radicals being independently of 1 to 5 carbon atoms, W is oxygen, sulphur or imino,
X is —CH$_2$—CH$_2$— or —CH=CH—(trans),
Y is —CH$_2$—CH$_2$— or —CH=CH—(cis or trans),
Z is -CH$_2$-CH$_2$- or

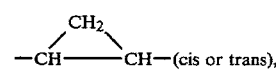

R$_1$ is alkyl of 1 to 10 carbon atoms or cycloalkyl of 3 to 9 carbon atoms,
R$_2$ is hydrogen or alkyl of 1 to 7 carbon atoms,
R$_3$ and R$_4$ are, independently, hydrogen, alkanoyl of 1 to 20 carbon atoms, or benzoyl, and
R is an ergolinylalkyl radical of formula II,

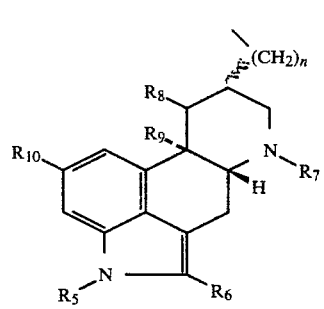

II wherein
n is 1 or 2,
R$_5$ is hydrogen, alkyl of 1 to 4 carbon atoms, or benzyl,
R$_6$ and R$_{10}$ are, independently, hydrogen or halogen,
R$_7$ is alkyl of 1 to 4 carbon atoms other than tert.butyl, and
(i) each of R$_8$ and R$_9$ is hydrogen, or
(ii) R$_8$ and R$_9$ together form a bond, or
(iii) R$_8$ is hydrogen, and
R$_9$ is alkoxy of 1 to 4 carbon atoms.

3. The compound of claim 2 wherein D is D$_4$.

4. The compound of claim 2 wherein D is D$_6$ and A is imidazolyl.

5. The compound of claim 2 wherein X is —CH=CH—(trans).

6. The compound of claim 2 wherein Y is —CH=CH—(cis) or —CH$_2$—CH$_2$.

7. The compound of claim 2 wherein Z is —CH$_2$—CH$_2$ or $$-CH\underset{}{\overset{CH_2}{\diagup\diagdown}}CH-(trans)-.$$

8. The compound of claim 2 wherein R$_1$ is alkyl of 1 to 10 carbon atoms.

9. The compunds of claim 2 wherein R$_2$, R$_3$ and R$_4$ each represent hydrogen, and OR$_3$ has the α-configuration.

10. The compound of claim 2 wherein W is oxygen or imino.

11. The compound of claim 2 wherein D is D$_3$ wherein 9-OR$_4$ is other than 9α-OH, D$_7$ or D$_8$.

12. The compound of claim 2 wherein W is sulphur.

13. The compound of claim 2 wherein W is oxygen, and R is a radical of the formula

II wherein
n is 1,
R$_7$ is methyl, and
R$_5$, R$_6$, R$_8$, R$_9$ and R$_{10}$ each represent hydrogen.

14. The compound of claim 2 wherein n is 2.

15. The compound of claim 2 wherein R$_5$ is alkyl of 1 to 4 carbon atoms or benzyl.

16. The compound of claim 2 wherein one or each of R$_6$ and R$_{10}$ is halogen.

17. The compound of claim 2 wherein R$_7$ is alkyl of 2 to 4 carbon atoms.

18. The compound of claim 2 wherein R$_8$ is hydrogen, and R$_9$ is alkoxy of 1 to 4 carbon atoms.

19. The compound of claim 2 wherein R$_3$ is alkanoyl.

20. The compound of claim 2 wherein W is imino and R is a radical of the formula

II wherein
n is 1,
R$_7$ is methyl and
R$_5$, R$_6$, R$_8$, R$_9$ and R$_{10}$ each represent hydrogen.

21. The compound of claim 2 in which Z is $$-CH\underset{}{\overset{CH_2}{\diagup\diagdown}}CH-(trans).$$

22. The compound of claim 2 in which D is D$_1$, D$_2$, D$_5$ or D$_6$.

23. The compound of claim 2 in which Y is —CH$_2$—CH$_2$—.

24. The compound of claim 2 in which Z is —CH$_2$—CH$_2$—.

25. The compound of claim 2 which is 15R-hydroxy-11α-imidazol-1'-yl-9-keto-16R-methyl-5-cis-prostenoic acid lysergyl ester.

26. The compound of claim 2 which is 11α,15R-dihydroxy-9-keto-16R-methyl-5-cis-prostenoic acid lysergyl ester.

27. The compound of claim 2 wherein R is an 8α-ergolinylalkyl radical.

* * * * *

UNITED STATES PATENT AND TRADEMARK OFFICE
CERTIFICATE OF CORRECTION

PATENT NO. : 4,249,001

DATED : February 3, 1981

INVENTOR(S) : Roland Wenger

It is certified that error appears in the above—identified patent and that said Letters Patent is hereby corrected as shown below:

Column 4, directly beneath line 1; delete the structural formula and substitute therefor the formula

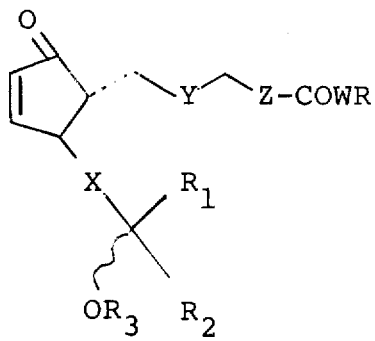

Claims 3-24 and 27, line 1 of each; change "The" to -- A --.

Column 16, Claim 20, directly beneath line 2; delete the structural formula and substitute therefor the formula

UNITED STATES PATENT AND TRADEMARK OFFICE
CERTIFICATE OF CORRECTION

PATENT NO. : 4,249,001
DATED : February 3, 1981
INVENTOR(S) : Roland Wenger

It is certified that error appears in the above—identified patent and that said Letters Patent is hereby corrected as shown below:

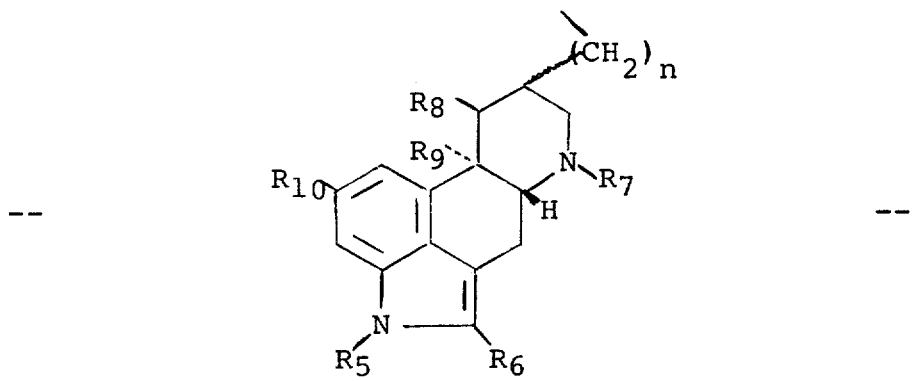

Signed and Sealed this

Twenty-second Day of February 1983

[SEAL]

Attest:

Attesting Officer

GERALD J. MOSSINGHOFF

Commissioner of Patents and Trademarks